United States Patent
Yokoyama et al.

[11] Patent Number: 5,876,371
[45] Date of Patent: Mar. 2, 1999

[54] INTRAVENOUS TUBE HOLDER

[76] Inventors: Lisa D. Yokoyama, 2307 Lisa Ct., Palatine, Ill. 60067; Donna J. Heller, 9741 N. Karlov; Cecilia S. Bato, 8624 Harding Ave., both of Skokie, Ill. 60076

[21] Appl. No.: 920,787

[22] Filed: Aug. 29, 1997

[51] Int. Cl.⁶ ........................................... A61M 5/00
[52] U.S. Cl. ........................ 604/80; 604/189; 128/DIG. 26
[58] Field of Search ................................. 604/80, 81, 82, 604/174, 189; 128/DIG. 26

[56] References Cited

U.S. PATENT DOCUMENTS

| | | |
|---|---|---|
| D. 243,477 | 2/1977 | Cutruzzula et al. . |
| D. 260,850 | 9/1981 | Greenblatt . |
| D. 263,624 | 3/1982 | Stenzler et al. . |
| D. 265,508 | 7/1982 | Rusteberg . |
| D. 269,121 | 5/1983 | Pollard . |
| D. 290,041 | 5/1987 | Scott . |
| 4,160,473 | 7/1979 | Winchell . |
| 4,397,641 | 8/1983 | Jacobs . |
| 4,453,933 | 6/1984 | Speaker . |
| 4,795,429 | 1/1989 | Feldstein ................................. 604/80 |
| 5,224,674 | 7/1993 | Simons ............................... 604/80 X |
| 5,316,246 | 5/1994 | Scott et al. . |
| 5,336,179 | 8/1994 | Ryan ...................................... 604/80 |

*Primary Examiner*—John D. Yasko
*Attorney, Agent, or Firm*—Niro, Scavone, Haller & Niro

[57] ABSTRACT

An intravenous tube holder for use in a trauma unit or similar environment is disclosed. The present invention includes at least one element, each element preferably containing a plurality of tracks, each track being design to secure a separate intravenous tube, said element further having a writing surface on the same side of the element as the tracks, with a writing surface next to each track for identifying the content and/or other dosage information identifying the contents of the intravenous tube therein. Each element further has a projection on the side opposite the tracks and writing surfaces for attaching the element to a support means. Each element has a male extension and female indent for interconnecting to additional element so as to accommodate a greater number of intravenous tubes.

7 Claims, 2 Drawing Sheets

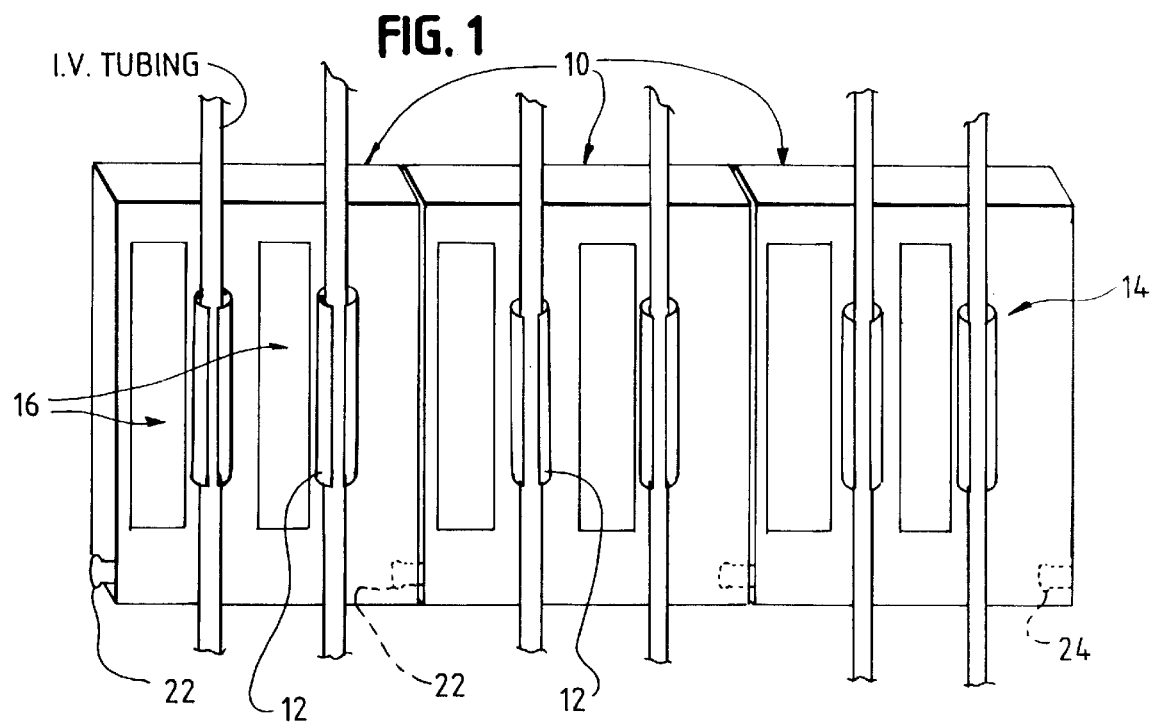
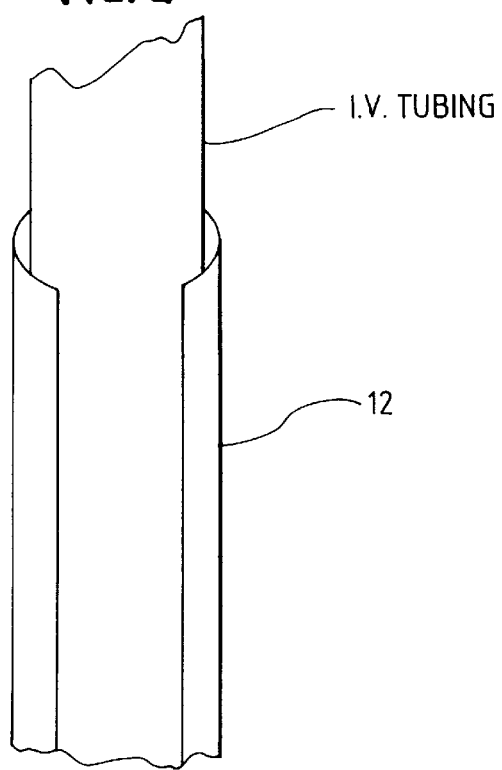

INTRAVENOUS TUBE HOLDER

BACKGROUND OF THE INVENTION

This invention relates generally to a device for organizing intravenous (IV) tubes in a trauma unit. Specifically, the present invention entails the use of individual, attachable elements having a track for releasably engaging one or more sections of tubing, each section of tubing representing a separate intravenous tube for a different source container, wherein the elements have a space for nonpermanent marking next to the track for identifying the medicine in the tubing, and the back portion of the element has a projection for engaging a C-clamp or similar mechanical support means.

The quick and accurate delivery of medicines and fluids to a patient is one of the most important aspects of trauma medical treatment. This delivery is typically via the use of a intravenous feed line which communicates various fluid from one or more solution bags or bottles to a hollow needle via a flexible tubing. The hollow needle is inserted into the patient's vein for the slow application of the therapeutic liquid. While this procedure is well known and normally operates without any complications, there are situations which make the monitoring of these fluids and their delivery very difficult.

In any hospital or other medical facility, the nursing staff is periodically relieved by the next shift. Since the nursing staff is responsible for monitoring the IV delivery, each new shift must become familiar quickly with the multitude of patients and the variety of IV drugs being administered. More importantly, in the case of an apparent adverse medicine reaction, the nursing staff or other medical personnel in the trauma unit must immediately be able to analyze the array of fluids administered to the patient. The ability to memorize each patients' array of medicines is impossible, given that a critical care nurse can have responsibility for dozens of different patients having intravenous attachments, each of them having anywhere from one to eight or more different IV drugs being administered. Currently, adhesive tape is added to the IV tube permitting the nurse to write information about the drug and its delivery. This means though that the nurse must adjust the often curled tape so that it can be read. As mentioned above, this arrangement is unsatisfactory if the nurse or other trauma unit personnel cannot identify the each of the respective tubes and their medicines quickly. If there is a variety of IV drugs being administered, their respective tubing often becomes entangled and confused. This entanglement may become life threatening if it takes the nurse time to identify which tube connects to which IV bottle. Even in the instances, where such delay is not life threatening to the patient, the quicker analysis and adjustment afforded by the present invention allows trauma nurses and other medical personnel to save time and thus focus more on patient care.

Another problem which may commonly occur is the problem of excess tubing. Health and safety guidelines for most hospitals currently prohibit intravenous tubes from touching the floor. In addition to the obvious risks of tripping both patients and personnel, the need to avoid touching the floor also is designed to lessen the danger of touch contamination.

In an attempt to clear away the confusion, a variety of inventions have been developed which try to keep the tubing orderly. One such approach is described by U.S. Pat. No. 4,160,473, entitled "Plastic Container with Auxiliary Tube Retention Means" issued to Winchell on Jul. 10, 1979. This device wraps the IV tube around the bag/bottle to take up the slack.

Unfortunately, this arrangement does not assist in marking of the IV tube. Further, this arrangement can injure the patient when the patient rolls or moves; the IV tube cannot "give" or expand so the needle is pulled out of the patient.

Other approaches have attempted to secure the IV tube through the use a clamp or support type of mechanism. Examples of these approaches include: U.S. Pat. No. Des. 260,850, entitled Medical Flexible Tube Support" issued to Greenblatt on Sep. 22, 1981; U.S. Pat. No. Des. 243,477, entitled "Intravenous Tube Anchor" issued to Cutruzzula et al. on Feb. 22, 1977; and, U.S. Pat. No. Des 263,624, entitled "Adjustable Medical Tubing Support Frame or Similar Article" issued to Stenzler et al. on Mar. 30, 1982.

In all of these approaches, the tube is secured but the marking of the tubing is even more difficult since these devices are bulky and complex.

Another approach has called for securing the IV tube to the patient through the use of a bracelet. This approach is exemplified by: U.S. Pat. No. 4,453,933, entitled "Intravenous Device" issued to Speaker on Jun. 12, 1984; U.S. Pat. No. Des 290,041, entitled "Intravenous Tube Holder" issued to Scott on May 26, 1987; and, U.S. Pat. No. 4,397,641, entitled "Catheter Support Device" issued to Jacobs on Aug. 9, 1983.

These devices focus upon preventing the IV needle from being pulled from the patient, in use, as the patient rolls, the pull on the tubing causes the IV bottle and support bracket to be pulled over. This is an even more dangerous situation than if the needle had been pulled out. More importantly, these devices to not facilitate the attachable addition of more intravenous tube elements, nor do they teach the easy identification of source solutions contained in various intravenous tubes. To the contrary, the placement of the tubes on a bracelet near the patient's wrist could complicate identification and removal of a particular tube under emergency conditions (e.g., a patient seizure could make analysis of drug identifications on a wrist bracelet virtually impossible).

In addition, a variety of devices have been designed to more securely affix the IV bottle. These include: U.S. Pat. No. Des 265,508, entitled "Combined Bottle Neck Clamp and Tube Holder" issued to Rusteberg on Jul. 20, 1982; and U.S. Pat. No. Des 269,121, entitled "Retractable IV Container Holder" issued to Pollard on May 24, 1983.

The basic structure of these patents result in the IV tubing being even less flexible since the tubing is more securely fastened to the IV bottle and support. These references, however, are not focused upon the easy engagement, disengagement, or identification of multiple intravenous tubes in a trauma setting.

U.S. Pat. No. 5,316,246 (Scott) employs a clip having an open face for identifying medicines being administered. Unfortunately, the preferred embodiment of this reference calls for a throughput for the intravenous tube and a plurality of clips for gathering excess tubing. The throughput hole defined in this reference is not conducive to easy remove or set up (as would be required in a trauma unit, and the multiple clips for each intravenous tube causes a bunching of tubes (and therefore a increased risk of mishandling) at the clip point. Also, this reference fails to provide identification of the medicines on the same side or face as the tubing, thus complicating the process of analyzing and removing tubes during the trauma treatment process. Finally, this reference has no ability to engage a mechanical support to limit entanglement and disorganization of the tubing during treatment or movement.

In short, none of the prior art, either alone or in combination, provides an intravenous tube holder for use in a trauma unit which can alternatively allow for the retention of multiple intravenous tubes and facilitates the quick and easy identification of the fluids in each respective tube.

SUMMARY OF THE INVENTION

The present invention employs an intravenous tube holder having one or more tracks for securing to an intravenous tube. These tracks are preferably open at one side, and have on the same side next to each track a marking area for identifying of each tube being held with marked adhesive paper or tape, or with an erasable grease pencil. These writing areas allow for entry of medical instructions and/or the attachment of a label giving identification and instructions as to the medicine being delivered via the intravenous tube, and is most preferably along a length of space next to each track so as to facilitate the quick analysis of a multiple IV tube set up. The element further has a projection for engaging with a C-clamp or other mechanical support means. Each track on each element permits a separate IV tube to be securely fastened, but, should quick removal or readjustment by the nurse be necessary, a "tug" on the IV tube readily releases the IV tube from its track.

In one embodiment of the invention, the space next to each track is color coded to provide quick identification of the medicine or its characteristics. This is particularly useful to designate "benign" liquids (e.g. saline solution) from critical medicines which may be subject to adverse reaction.

Each element has a "lock and key" arrangement to facilitate multiple element arrays where a greater number of IV tubes is required. Each element has a key which engages in a frictional "snap fit" in the lock portion of another element. Thus the elements can be joined to create virtually an infinite sequence. Each element preferably contains approximately two to four tracks, but, the number of tracks may be adjusted to fit the practice of the hospital and the preference of the manufacturer.

The holders are constructed from a variety of materials obvious to those of ordinary skill in the art. These materials preferably include a variety of rigid plastics. Alternatively, the invention can be constructed of a readily biodegradable material having high rigidity and strength, thus permitting the invention, once it is disposed in a land-fill of the like, to readily breakdown. This aspect reduces problems for the hospital when faced with disposal used or broken holders.

The invention, together with various embodiments thereof, will be more fully explained by the following drawings and their descriptions.

DESCRIPTION OF THE DRAWINGS

The novel features which are characteristic of the invention are set forth in the appended claims. The invention itself, however, together with further objects and attendant advantages thereof, will be best understood by reference to the following description taken in connection with the accompanying drawings, in which:

FIG. 1 is a frontal view of three interconnected elements showing the preferred embodiment of the invention.

FIG. 2 illustrates a detail of a track of the preferred embodiment of the present invention.

DETAILED DESCRIPTION OF THE PREFERRED EMBODIMENT

Figure 3:
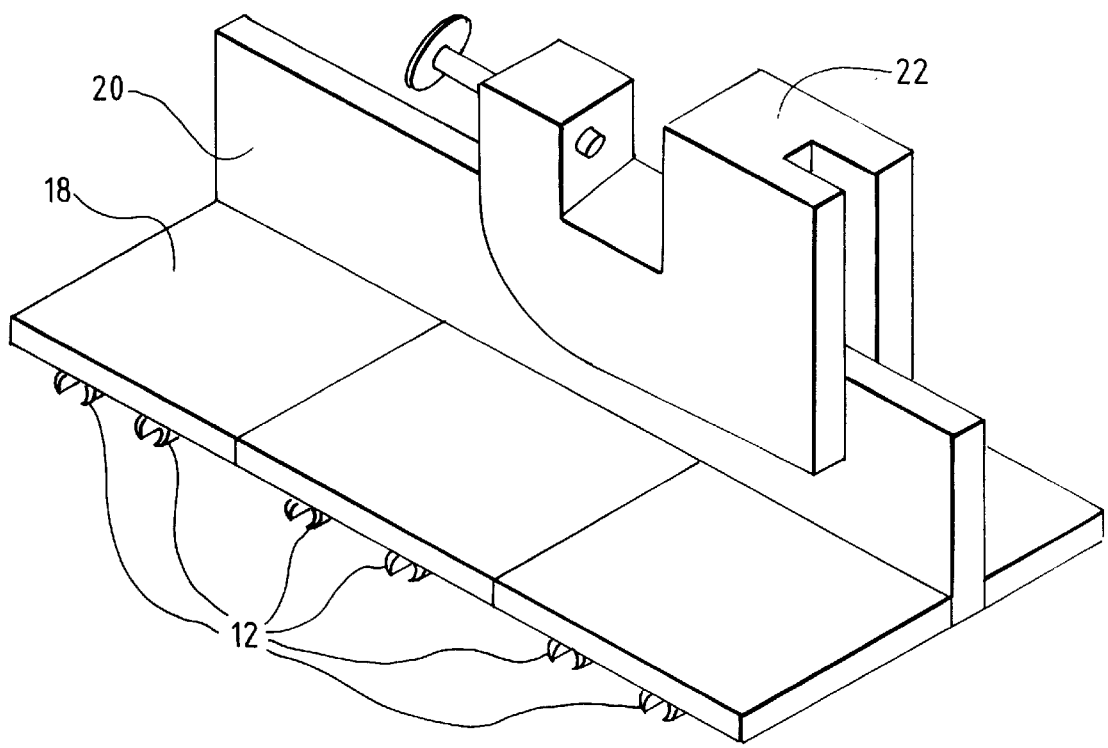
FIG. 3 is a rear perspective view of the projection element of the present invention in use with a C-clamp.

FIG. 1 is a frontal view of the preferred embodiment of the invention. The present invention comprises one or more elements 10, each of which has a plurality of tracks 12 on a front surface 14. As shown in FIG. 2, the tracks 12 project outward from the front surface 14 and define a partial annulus. The tracks 12 are preferably at least about 1 inch in length and are structured such that each individual track provides sufficient frictional clasping of a separate IV tube to prevent the tubing from falling away, but not so much friction that the tubing is not readily released upon movement by the patient.

Each element 10 of the present invention is preferably designed to accommodate two or more IV tubes drain into a common feeder tube. Labeling of the tubes (and hence their solutions) becomes critical should it become necessary to trace a drug which is causing a negative reaction. Thus, a strip or marking surface 16 is provided along the length next to each track for identification of the medicine and/or dosage instructions for the contents of each tube. Each of the tracks 12 are separated by about 1 to 1½ inches so as to create the space for the marking surface. Most preferably, this strip is made of a suitable plastic for marking upon with a grease pencil or marker and can be erased through the use of a cloth or alcohol wipe in order to accommodate changes in medicine to a patient (the most preferred embodiment of this invention, though, is intended to be disposed after use with a single patient, thus reducing the risk of spreading infectious matter). Alternatively, the strip can receive a plain pencil marking, or can even comprise a strip for receiving adhesive written instructions and/or other identification material on masking tape.

In a second alternative embodiment, the writing surface 16 is replaced and/or augmented with a color coding for quickest analysis and identification. For example, in this embodiment, a red holder would signify a particular drug that requires close monitoring (e.g., dilantin). Other, commonly used benign liquids (such as saline solution) might be given green, blue, or some other color not typically associated with danger. One potential drawback of this system, however, would be the limitation on identifying specific drugs or tube contents based upon the limitation of color types. Thus, a variant of this alternative embodiment would use limited colors (such as red) in addition to the written surface 16 in order to connote a special warning signal to the nurse or other medical professional that the medicine in question requires close monitoring.

As shown in FIG. 3, the an opposite or rear side 18 of each element 10 has a projection 20. Projection 20 is suitable for engaging a C-clamp 22, or similar mechanical support means, wherein the support is, in turn, attached to a patient bed railing, IV stand, or similar location (not shown). The specific placement of the projection 20 and C-clamp 22 should be left to the judgment of the nurse or other medical professional, but it should be understood that it placement should ensure that: 1) the tubing stays off the floor; 2) the location of the elements preferably stays away from interference or dislodgement by the patient; and 3) the writing surface 16 is easily visible to the trauma unit staff.

As can be seen by reference again to FIG. 1, each element 10 of the present invention is designed to interlock or connect with another identical element 10 in order to accommodate additional IV tubes. This interconnecting feature is accomplished by a "lock and key" engagement of each element. Each element 10 has a male extension 22 which is designed to interlock with a reciprocal female indent 24. This male\female connection, in theory, would facilitate the ad infinitum extension of elements 10 to accommodate a limitless number of IV tubes. The male\female connection is designed to support each of the elements such that only C-clamp would be necessary to support a single projection 20. A more secure, stable support could be provided, however, by placing a C-clamp or similar connection on each projection 20, thus offering direct support means for each element. This interconnective feature would be particularly useful in facilitating the addition of a "hot" or "crash" line for quickly administering drugs, such as antibiotics, on a "push line" so as to avoid incompatibility with other drug lines already in place.

Of course, it should be understood that various changes and modifications to the preferred embodiments described herein will be apparent to those skilled in the art. For instance, each element can be designed to have one, three, four, or more tracks for accommodating a different number of IV tubes. Nor do the advantages and uses of the present invention need to be limited to trauma usage—other units can easily benefit from the speed, convenience, and simplicity offered by the present device. Such changes and modifications to the use and design of the present invention can be made without departing from its the spirit and scope and without diminishing its attendant advantages. It is, therefore, intended that all such changes and modifications be covered by the following claims.

What is claimed is:

1. An intravenous tube holder for securing an intravenous tube to a support means, said intravenous tube holder comprising an element having a front face and a back face, said front face having a track defined thereon for receiving a single intravenous tube, said front face further comprising a writing surface defined next to said track for identifying the contents and/or dosage instructions for the intravenous tube contained in said track, said element further comprising a male extension and a female indent, said extension and indent for receiving a male extension from a different element and said extension for connecting said element to a another element, said element further comprising a projection defined on said rear face for securing said element to said support means.

2. The intravenous tube holder according to claim 1 further comprising a plurality of tracks defined on said front face of said element.

3. The intravenous tube holder according to claim 2 wherein said labeling surface accepts grease pencil or erasable marker.

4. The intravenous tube holder according to claims 1 or 3 wherein said writing surface is color-coded.

5. An intravenous tube holder for securing an intravenous tube to a support means, said intravenous tube holder comprising a plurality of elements, each of said elements having:

a) a front face;
   b) a back face;
   c) a first end;
   d) a second end;
   e) a plurality of tracks defined on said front face, each of said tracks engaging a separate, single intravenous tube,
   f) a writing surface on front face parallel to each of said plurality of tracks;
   g) a projection on said rear face, said projection adapted for detachably connecting with said support means;
   h) a male extension located on said first end; and
   i) a female indent located on said second; whereby said male extension connects to a female indent of another element and sale female indent is adapted for receiving a male extension from a different element.

6. The intravenous tube holder according to claim 2 wherein said labeling surface accepts grease pencil or erasable marker.

7. The intravenous tube holder according to claims 5 or 6 wherein said writing surface is color-coded.

* * * * *